(12) United States Patent
Okada (10) Patent No.: US 11,510,701 B2
(45) Date of Patent: Nov. 29, 2022

(54) SEMEN STORAGE CONTAINER (71) Applicant: Hirokazu Okada, Minoo (JP)

(72) Inventor: Hirokazu Okada, Minoo (JP)

(*) Notice: Subject to any disclaimer, the term of this patent is extended or adjusted under 35 U.S.C. 154(b) by 630 days.

(21) Appl. No.: 16/338,722

(22) PCT Filed: Oct. 2, 2017

(86) PCT No.: PCT/JP2017/035826
§ 371 (c)(1),
(2) Date: Apr. 2, 2019

(87) PCT Pub. No.: WO2018/066514
PCT Pub. Date: Apr. 12, 2018

(65) Prior Publication Data
US 2021/0282815 A1 Sep. 16, 2021

(30) Foreign Application Priority Data
Oct. 3, 2016 (JP) .............................. JP2016-195665

(51) Int. Cl.
*A61B 17/43* (2006.01)
(52) U.S. Cl.
CPC .................................... *A61B 17/43* (2013.01)
(58) Field of Classification Search
CPC ............ A61B 10/0045; A61B 10/0058; A61B 10/0096; A61B 17/43; A61B 17/425;
(Continued)

(56) References Cited

U.S. PATENT DOCUMENTS 4,862,674 A * 9/1989 Lejondahl ............ B65D 81/386
53/432
2004/0157205 A1 8/2004 Etheredge, III et al.
(Continued)

FOREIGN PATENT DOCUMENTS

CN 201088709 Y 7/2008
CN 201320292 Y 10/2009
(Continued)

OTHER PUBLICATIONS

Chinese Notification of First Office Action, dated Nov. 29, 2019, for Chinese Application No. 2017800742681, and its English translation.
(Continued)

*Primary Examiner* — Carrie R Dorna
(74) *Attorney, Agent, or Firm* — Barnes & Thornburg LLP; Jeffrey R. Stone (57) ABSTRACT

A semen storage container which can store semen in a favorable state, into which semen is easily put and out of which semen is easily taken, is provided. A semen storage container includes an outer case having an open upper end, an inner case, the inner case having an opening portion at an upper end and being provided on an inner side of the outer case to close an opening of the outer case, and a removable lid laid over an upper end portion of the outer case to close the opening portion. The inner case includes a semen guide which communicates with the opening portion at the upper end and has an inner circumferential surface provided as an inclined surface which spreads upward and a cylindrical semen pool which communicates with an opening portion at a lower end of the semen guide and includes a tapered bottom portion.

7 Claims, 9 Drawing Sheets

(58) Field of Classification Search
CPC ....... A61B 17/435; A61B 19/02; A61B 19/00; A61B 19/022; A61B 19/027; A61B 19/024; A61B 19/021; A61B 19/025; B01L 3/50; B01L 3/5088; B01L 3/52; B01L 3/527; B01L 2400/0457; B01L 2300/0848; B01L 2300/0858; B01L 2200/0636; B01L 2200/0647; B01L 3/50851; B01L 2300/08; B01L 2200/00; A61J 1/05; A61J 1/1412; A61J 1/1425; A61D 19/00; A61D 19/02; A61D 19/021; A61D 19/022; A61D 19/024; A61D 19/025; A61D 19/027; C12M 1/24; C12M 23/00

See application file for complete search history.

(56) References Cited

U.S. PATENT DOCUMENTS

| | | | |
|---|---|---|---|
| 2006/0228794 | A1 | 10/2006 | Ranoux et al. |
| 2007/0031895 | A1* | 2/2007 | Herr .................. A61B 10/0058 435/7.2 |
| 2012/0052485 | A1 | 3/2012 | Shany et al. |
| 2013/0225387 | A1 | 8/2013 | Hirai et al. |
| 2017/0239652 | A1 | 8/2017 | Shan |

FOREIGN PATENT DOCUMENTS

| | | | | |
|---|---|---|---|---|
| CN | 201476987 | U | * 5/2010 | |
| CN | 201476987 | U | 5/2010 | |
| CN | 204863299 | U | 12/2015 | |
| CN | 205525873 | U | 8/2016 | |
| CN | 106053142 | A | 10/2016 | |
| CN | 106859813 | | * 6/2017 | ........... A61D 19/021 |
| JP | 28-10558 | U | 10/1953 | |
| JP | S62-006843 | | 1/1987 | |
| JP | 05-035110 | U | 5/1993 | |
| JP | 3082473 | U | 12/2001 | |
| JP | 2012115829 | | 6/2012 | |
| WO | WO-2009123889 | A1 * | 10/2009 | ........... A61D 19/022 |
| WO | WO-2014192919 | A1 * | 12/2014 | .......... B01L 3/50825 |

OTHER PUBLICATIONS

Extended European Search Report issued in EP Application No. 17858352.2, dated Apr. 29, 2020.

Naka ivf Device 70-cc Semen Collection Container, searched on Jun. 13, 2016, the Internet, http://www.nakamedical.co.jp/pdf_img/201409/ivf/cata/nm4370s.pdf (with partial English translation).

Notice of Grounds of Rejection, dated Nov. 20, 2018 in Patent Application 2018-502189.

* cited by examiner

SEMEN STORAGE CONTAINER

TECHNICAL FIELD

The present invention relates to a semen storage container and particularly to a semen storage container which can store semen in a favorable state, into which semen is easily put and out of which semen is easily taken.

BACKGROUND ART

In fertility treatment of humans, general semen testing (including artificial insemination) in which sperm or ovum is manipulated and assisted reproductive technology (ART) have widely been performed. Semen of humans used for general semen testing or ART is once stored in a container after collection and sent to a site such as a hospital where general semen testing or ART is performed.

Figure 9:
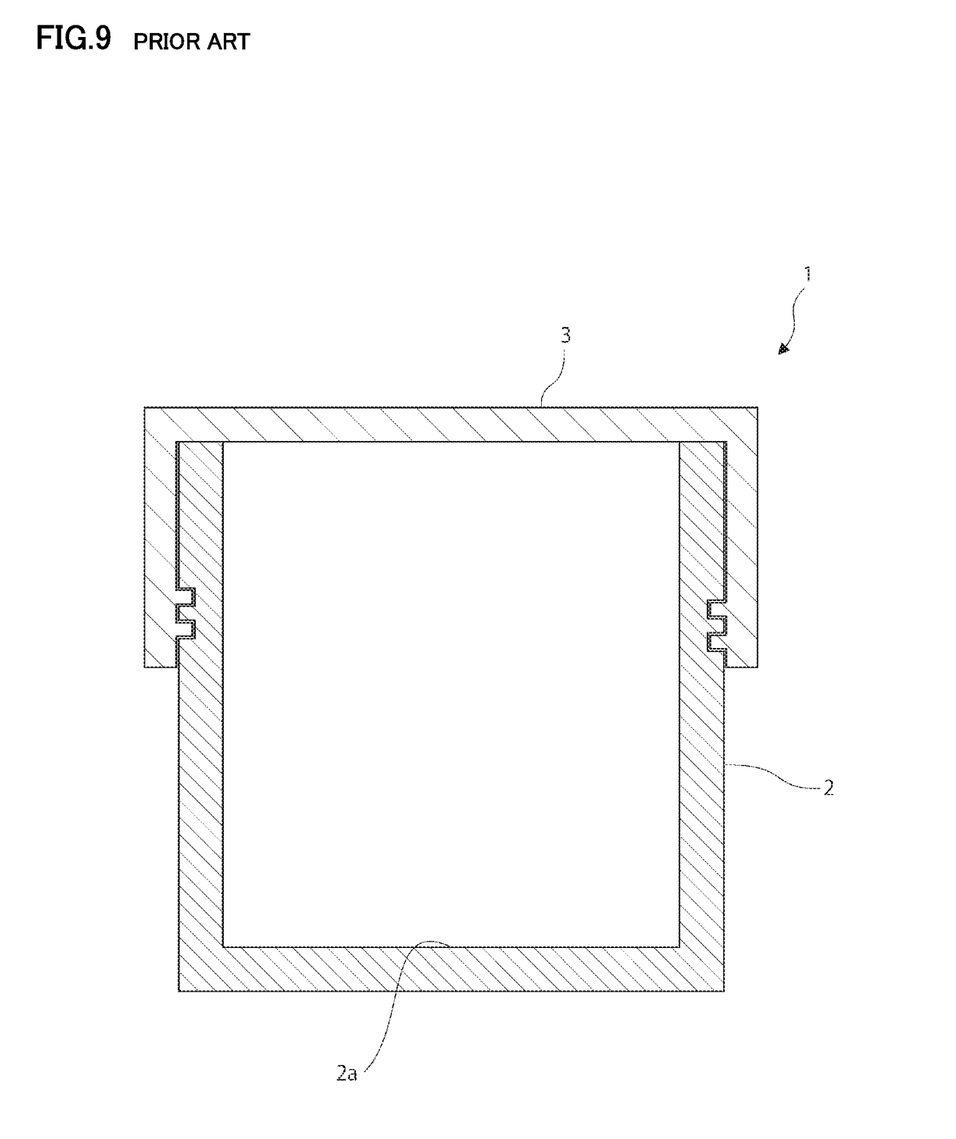
FIG. 9 is a cross-sectional view showing a conventional example.

A container 1 shown in FIG. 9 has conventionally been used as a container for storing semen. Container 1 includes a lid 3 attached to a cylindrical main body 2 with a bottom surface 2a. Collected semen is accommodated in main body 2 and hermetically sealed by lid 3 (see, for example, NPL 1).

CITATION LIST

Non Patent Literature

NPL 1: NAKA ivf Device 70 cc semen collection container, searched on Jun. 13, 2016, the Internet, http://www.naka-medical.co.jp/pdf_img/201409/ivf/cata_nm4370s.pdf

SUMMARY OF INVENTION

Technical Problem

In the conventional example, when an amount of collected semen is small and when an area of bottom surface 2a of cylindrical main body 2 is large relative to the amount of semen, semen spreads over bottom surface 2a after it is accommodated in main body 2 of the container. Then, an area of a liquid surface in contact with air increases, a water content evaporates, and performance of semen tends to lower. When the area of bottom surface 2a of main body 2 is made smaller to make the area of the liquid surface in contact with air smaller in order to avoid this, an opening of main body 2 of container 1 becomes smaller. Then, it becomes difficult to put semen into container 1.

Semen accommodated in container 1 is taken out by being suctioned by a pipet or the like. In container 1 in the conventional example, however, as an amount of semen remaining in container 1 decreases, semen spreads over bottom surface 2a while container 1 perpendicularly stands. Then, semen cannot completely be taken out with the pipet, and should be taken out by tilting container 1 to collect the semen at an end portion of container 1, which is bothersome.

The present invention was made with attention being paid to the problems above, and it relates to a semen storage container which can store semen in a favorable state, into which semen is easily put and out of which semen is easily taken.

Solution to Problem

A semen storage container according to the present invention includes an outer case with bottom in a cylindrical shape having an open upper end, an inner case with bottom, the inner case having an open upper end and being provided on an inner side of the outer case to close an opening portion at the upper end of the outer case, and a removable lid laid over an upper end portion of the outer case to close an opening portion at the upper end of the inner case. The inner case includes a semen guide which communicates with the opening portion at the upper end and has an inner circumferential surface provided as an inclined surface which spreads upward and a cylindrical semen pool which communicates with an opening portion at a lower end of the semen guide and includes a tapered bottom portion. The object above is achieved by this semen storage container.

According to the construction, semen is introduced from the opening portion at the upper end of the inner case, guided by the inclined surface on an inner circumference of the semen guide, and stored in the semen pool. The semen guide is in a shape of an inverted frustum and the semen pool is provided at the lower end of the semen guide. Therefore, a horizontal cross-section of the semen pool (the horizontal cross-section being a surface cut along a surface orthogonal to a vertical direction) is smaller in area than the opening portion of the outer case and the inner case. Therefore, when semen is stored in the semen pool, an area of a liquid surface in contact with air is small. Then, even when an amount of collected semen is small, lowering in performance of semen due to evaporation of a water content can be prevented and semen can be stored in a favorable state. In particular, when an amount of semen is small and semen is stored only at the bottom portion of the semen pool, semen can be stored in a favorable state because the bottom portion is tapered and an area of the liquid surface in contact with air is small relative to the amount of semen.

Since the inner circumferential surface of the semen guide is provided as the inclined surface which spreads upward, semen can readily be put into the container by setting an area of the opening portion at the upper end of the inner case.

Furthermore, the semen pool has the tapered bottom portion. Therefore, even though an amount of semen remaining in the container is small in taking out semen with a pipet or the like, semen can be stored at the bottom portion and readily taken out of the container without tilting the container.

The tapered shape means such a shape that an area of the horizontal cross-section decreases downward, and is exemplified by a shape of an inverted cone, a shape of an inverted frustum, and a hemispherical shape projecting downward.

In one embodiment of this invention, the semen pool includes a cylindrical body portion, and the body portion has an upper end continuous to the opening portion at the lower end of the semen guide.

By providing the semen pool as being continuous to the semen guide, the shape of the inner case is simplified. The semen pool, however, does not necessarily have to be provided as being continuous to the semen guide.

In a preferred embodiment, the semen pool includes a cylindrical body portion, the body portion has a diameter not greater than 30 mm, and an amount of accommodation of semen is set to be not less than 10 mL and not more than 20 mL. More preferably, an amount of accommodation of semen is set to at least 12.5 mL.

An amount of semen collected from a human at a time has been said as being from 0.1 mL to 10 mL. Therefore, according to the construction above, all semen collected at a time can be accommodated in the semen pool without increasing an area of a liquid surface in contact with air.

In a preferred embodiment, the semen pool is provided with scales.

By providing scales, an amount of semen stored in the semen pool can be known at a glance.

The scales are preferably provided in 1.0 mL increments.

In a more preferred embodiment, a gap between the inner case and the outer case is defined as a hermetically sealed space surrounding the inner case, and any of air, a liquid, a heat insulating material, a thermal storage material, and a heat retention material is accommodated in the hermetically sealed space. The hermetically sealed space serves as any of an air layer, a liquid layer, a heat insulating layer, a thermal storage layer, and a heat retention layer.

In order to maintain favorable performance of semen, abrupt variation in temperature is desirably not applied to semen accommodated in the container. Since any of the air layer, the liquid layer, the heat insulating layer, the thermal storage layer, and the heat retention layer is provided on an outer side of the inner case where semen is accommodated, outdoor air temperature or a temperature of a hand when the outer case is held with the hand is less likely to conduct to semen and application of abrupt variation in temperature to semen can be prevented.

Water may be adopted as a liquid to be accommodated in the hermetically sealed space. In this case, preferably, a temperature of water is set to be not lower than 15 degrees and not higher than 37 degrees, preferably not lower than 20 degrees and not higher than 37 degrees, and more preferably not lower than 20 degrees and not higher than 25 degrees.

By setting water to the temperature above, variation in temperature of semen from the time point of collection of semen and accommodation in the container according to the present invention until use can be gentle. Semen is considered as desirably being stored at a temperature not lower than 20 degrees and not higher than 25 degrees. Therefore, by setting a temperature of water in particular to be not lower than 20 degrees and not higher than 25 degrees, semen accommodated in the container can be maintained at a temperature not lower than 20 degrees and not higher than 25 degrees for a period as long as possible and semen can be stored in a favorable state.

The hermetically sealed space between the inner case and the outer case is preferably hermetically sealed to maintain hermeticity.

According to the construction above, air, a liquid, a heat insulating material, a thermal storage material, or a heat retention material accommodated in the hermetically sealed space does not leak. Even when a volatile substance which may degrade performance of semen is used for the heat insulating material, the thermal storage material, or the heat retention material, the volatile substance does not leak from the hermetically sealed space and degradation of performance of semen can be prevented.

In one embodiment, the semen pool is separable from the semen guide, and a connection portion is provided in the semen pool and the semen guide.

Normally, collected semen is transferred to a test tube, which is in turn set, for example, onto treatment equipment such as a centrifuge. According to the construction, however, by shaping and sizing the semen pool in conformity with treatment equipment, the semen pool where semen is accommodated can be separated from the semen guide and directly set on the treatment equipment. Therefore, transfer of semen to the test tube for setting onto the treatment equipment does not have to be performed and operations can be more efficient. Furthermore, contamination of semen in transfer to the test tube can be prevented.

The semen storage container according to the present invention may further include a cylindrical supplemental cover for assisting collection of semen, and the supplemental cover may include an insertion portion supported as being inserted into the inner case and a cover portion which protrudes through an opening at the upper end of the inner case.

According to the construction, the cover portion of the supplemental cover can prevent semen from scattering in collection of semen so that an amount of collectable semen can be increased.

The inner case may removably be attached to the outer case or fixed to the outer case by welding or bonding.

When the inner case is removably attached to the outer case, a user may remove the inner case, place a liquid at a desired temperature in the outer case, and attach the inner case to the outer case. Thus, a liquid at a desired temperature can be accommodated in the hermetically sealed space immediately before use of the container according to the present invention so that semen can be stored in a favorable state.

Alternatively, when the inner case is fixed to the outer case, hermeticity of the hermetically sealed space can reliably be kept.

Advantageous Effects of Invention

According to the present invention, the horizontal cross-section of the semen pool is smaller in area than the opening portion at the upper end of the outer case and the inner case. Therefore, when semen is accommodated in the semen pool, an area of a liquid surface in contact with air is small relative to an amount of semen. Then, lowering in performance of semen due to evaporation of a water content can be prevented so that semen can be stored in a favorable state. Since the semen guide having the inclined inner circumferential surface which spreads upward is provided, semen can easily be put into the container. Furthermore, the semen pool has the tapered bottom portion. Therefore, in taking out semen with a pipet or the like, even though an amount of semen remaining in the container is small, semen can be stored at the bottom portion and can readily be taken out of the container without tilting the container.

DESCRIPTION OF EMBODIMENTS

An embodiment of the present invention will be described with reference to the drawings.

Figure 1:
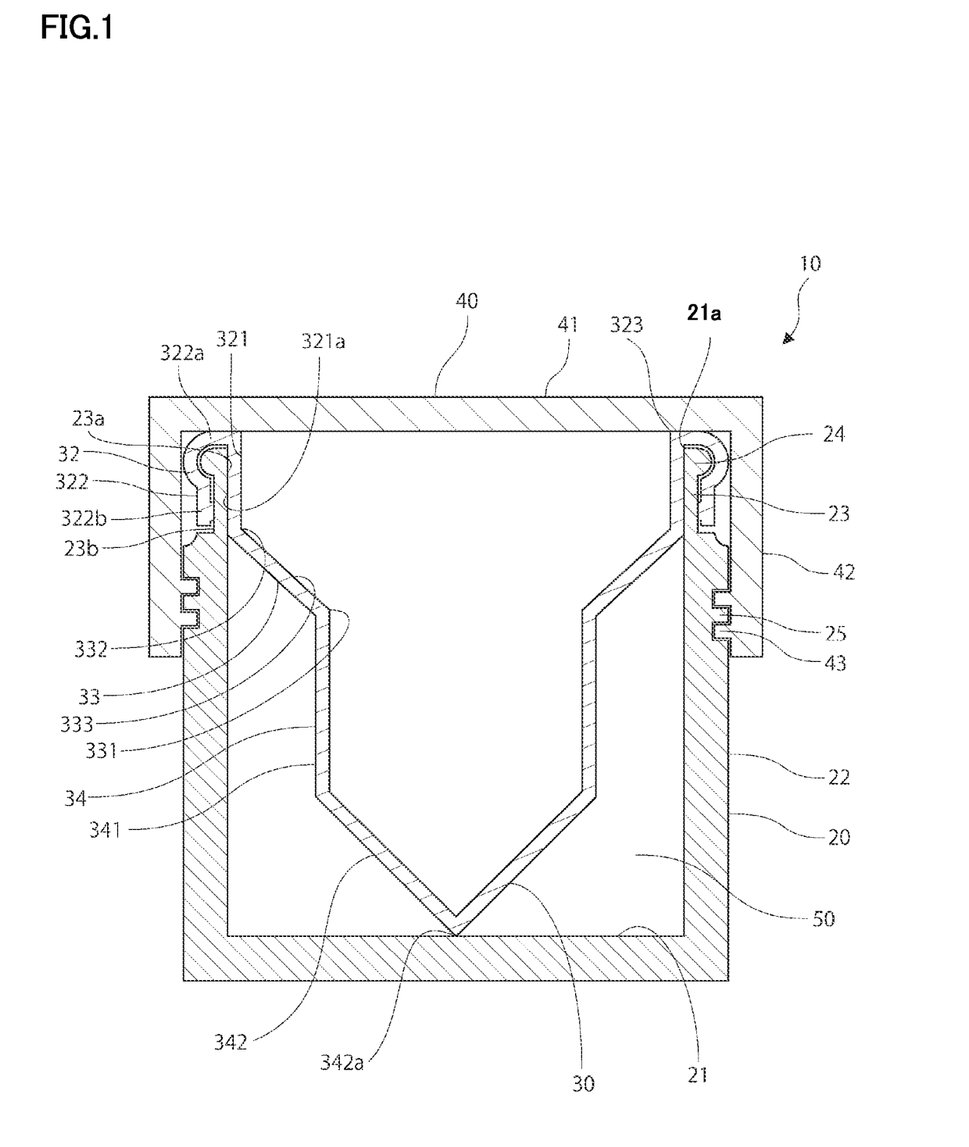
FIG. 1 is a cross-sectional view of a semen storage container according to one embodiment of the present invention.

FIG. 1 shows a semen storage container 10 according to one embodiment of the present invention.

Semen storage container 10 is constituted of a cylindrical outer case 20 which has an open upper end and a bottom surface 21, an inner case 30 with bottom which has an open upper end and is provided on an inner side of outer case 20, and a removable lid 40 laid over an upper end portion of outer case 20 to close an opening portion 323 at the upper end of inner case 30.

In outer case 20, an upper end portion 23 of an outer circumferential wall 22 is smaller in outer diameter than other portions of outer circumferential wall 22. A fitting projecting edge 24 fitted to a fitting portion 32 of inner case 30 is formed around an upper end of an outer circumferential surface 23b of upper end portion 23.

A thread 25 to be screwed to a thread 43 formed in an inner circumferential surface of lid 40 is formed below upper end portion 23 in an outer circumferential surface of outer circumferential wall 22.

Inner case 30 is attachable to and removable from outer case 20 and it includes fitting portion 32 fitted to upper end portion 23 of outer case 20, a semen guide 33 continuous to a lower portion of fitting portion 32, and a cylindrical semen pool 34 which is continuous to an opening portion 331 at a lower end of semen guide 33 and includes a tapered bottom portion 342.

Fitting portion 32 includes a cylindrical fitting portion main body 321 which includes opening portion 323 at an upper end and a fold-back portion 322 folded back from an upper end of fitting portion main body 321 toward an outer side of upper end portion 23 of outer case 20.

Fold-back portion 322 is provided around an outer circumference of fitting portion main body 321 and it includes a fitting recess 322a fitted to fitting projecting edge 24 at the upper end of outer case 20 and a circumferential wall 322b extending downward from a tip end of fitting recess 322a.

Fold-back portion 322 is flexible to such an extent that upper end portion 23 of outer case 20 can be inserted in between fold-back portion 322 and fitting portion main body 321. As fitting projecting edge 24 of outer case 20 is fitted to fitting recess 322a in inner case 30, inner case 30 is fitted to opening portion 21a at the upper end of outer case 20 from the inner side. While inner case 30 is fitted to outer case 20, outer circumferential surface 321a of fitting portion main body 321 is in intimate contact with inner circumferential surface 23a of upper end portion 23 of outer case 20 to stabilize fitting between inner case 30 and outer case 20.

Semen guide 33 has an inner circumferential surface as an inclined surface 333 which spreads upward and exhibits a shape of an inverted frustum of a cone. An opening portion 332 at an upper end is continuous to the lower end of fitting portion main body 321 and guides semen introduced from opening portion 323 of fitting portion 32 toward semen pool 34 along inclined surface 333 of semen guide 33.

Semen pool 34 stores semen guided by semen guide 33. The semen pool includes a cylindrical body portion 341 formed as being continuous to opening portion 331 at a lower end of semen guide 33. A bottom portion 342 in a shape of an inverted cone is formed at a lower end of body portion 341. A lower end 342a of bottom portion 342 abuts on bottom surface 21 of outer case 20 so that a state of fitting of inner case 30 to outer case 20 can be maintained in a stable manner.

Figure 2:
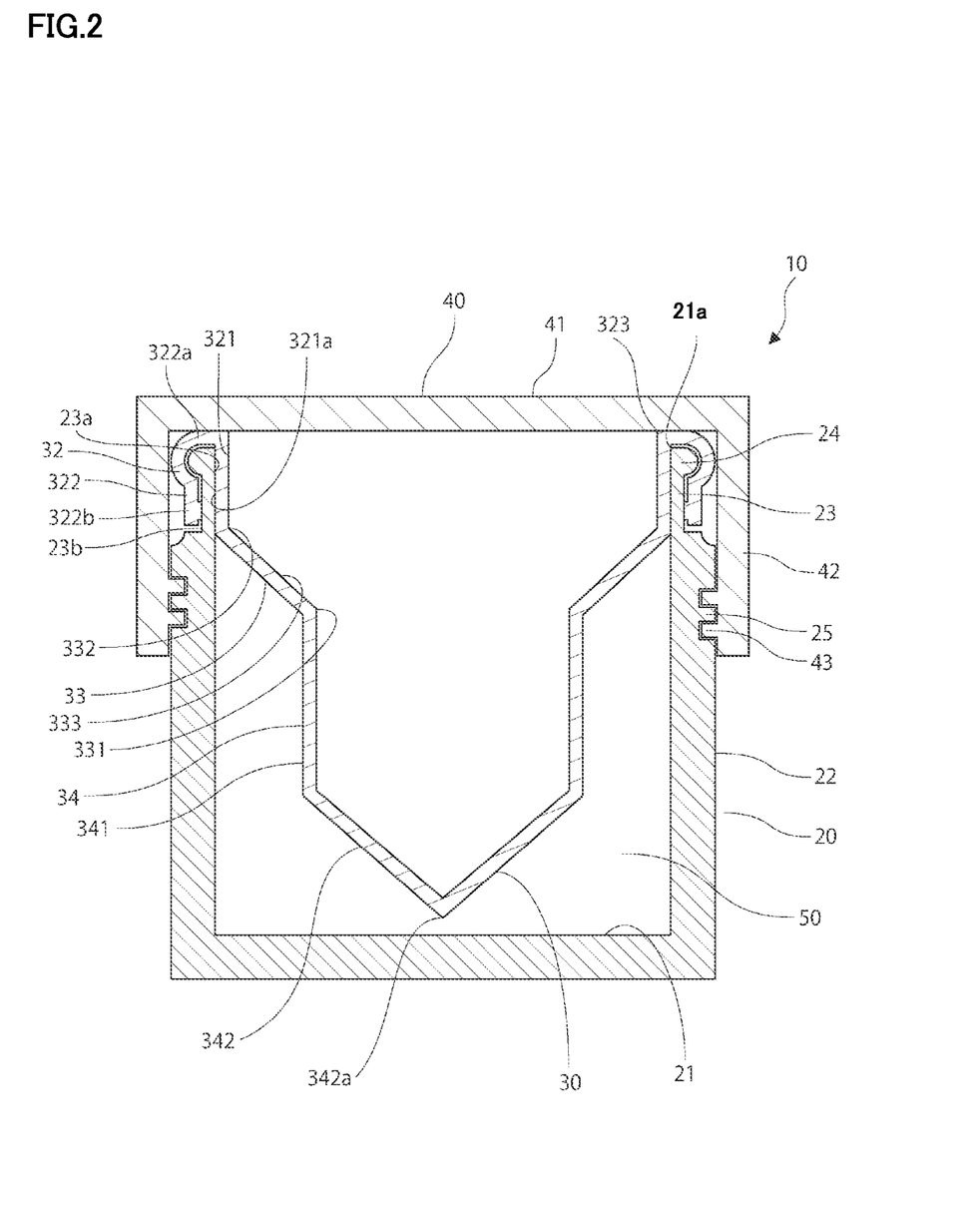
FIG. 2 is a cross-sectional view showing another example of the semen storage container.

Lower end 342a of bottom portion 342 does not necessarily have to abut on bottom surface 21 of outer case 20 but may be located above bottom surface 21 of outer case 20 as shown in FIG. 2.

An outer surface of bottom portion 342 and body portion 341 of semen pool 34 may be provided with scales (not shown) in 1.0 mL increments. In this case, outer case 20 and inner case 30 are transparent to such an extent that scales and an amount of semen accommodated in semen pool 34 can externally visually be recognized.

Bottom portion 342 may be shaped into an inverted frustum of a cone. In this case, a lower surface of bottom portion 342 may abut on bottom surface 21 of outer case 20.

By fitting inner case 30 to outer case 20, a gap between inner case 30 and outer case 20 is defined as a hermetically sealed space 50 which has hermeticity and surrounds inner case 30. Air is confined in hermetically sealed space 50 to implement a heat insulating layer.

Instead of air, a liquid such as water, a heat insulating material, a thermal storage material, or a heat retention material may be accommodated in hermetically sealed space 50. A heat insulating material, a thermal storage material, or a heat retention material which does not produce a volatile substance is preferred for avoiding degradation of performance of semen, and it is composed of a material such as polypropylene (PP) or polyethylene (PE) without being limited. When water is accommodated in the hermetically sealed space, a temperature of water may be set to be not lower than 15 degrees and not higher than 37 degrees, preferably not lower than 20 degrees and not higher than 37 degrees, and more preferably not lower than 20 degrees and not higher than 25 degrees.

In order to enhance hermeticity of hermetically sealed space 50, a thread for screwing may be formed in outer circumferential surface 321a of fitting portion main body 321 and inner circumferential surface 23a of upper end portion 23 of outer case 20.

In the present embodiment, in inner case 30, a diameter of fitting portion main body 321 of fitting portion 32 is set to 50 mm, a diameter of opening portion 332 at the upper end of semen guide 33 is set to 50 mm, a diameter of opening portion 331 at the lower end of semen guide 33 is set to 30 mm, a diameter of body portion 341 of semen pool 34 is set to 30 mm, a height (a vertical length) of fitting portion main body 321 is set to 20 mm, a height of semen guide 33 is set to 15 mm, a length of body portion 341 of semen pool 34 is set to 20 mm, and a height of bottom portion 342 of semen pool 34 is set to 15 mm. In this case, an amount of accommodation of semen in semen pool 34 is 17.7 mL.

A dimension of inner case 30 is not limited as above. A diameter of cylindrical body portion 341 of semen pool 34 should only be set to 30 mm or smaller and an amount of accommodation of semen should only be set to be not less than 10 mL and not more than 20 mL and more preferably to at least 12.5 mL.

Lid 40 is constituted of a top plate portion 41 and an outer circumferential wall 42 formed around top plate portion 41, and thread 43 to be screwed to thread 25 of outer case 20 is formed at a lower end portion of an inner circumferential surface of outer circumferential wall 42. An outer circumferential surface of outer circumferential wall 42 of lid 40 may be knurled for preventing slipping.

Inner case 30, outer case 20, and lid 40 are composed of polypropylene (PP), and lid 40 is formed by injection molding of a synthetic resin composed of polyethylene (PE) or the like. A material for the synthetic resin is not limited as such. Semen storage container 10 is manufactured by assembling inner case 30, outer case 20, and lid 40. In assembly, initially, upper end portion 23 of outer case 20 is inserted in between fold-back portion 322 of fitting portion 32 of inner case 30 and fitting portion main body 321. Then, fitting projecting edge 24 of outer case 20 is fitted to fitting recess 322a of fitting portion 32 of inner case 30. Inner case 30 is thus fitted into outer case 20. Then, lid 40 is attached by screwing thread 43 of lid 40 to thread 25 of outer case 20. While lid 40 is attached to outer case 20, fitting portion 32 of inner case 30 is pressed against outer case 20 from above by lid 40. Therefore, fitting projecting edge 24 of outer case 20 does not come off fitting recess 322a of fitting portion 32 of inner case 30 and lid 40 reliably closes opening portion 323 in fitting portion 32 of inner case 30.

According to semen storage container 10 in the present embodiment, an area of the horizontal cross-section of semen pool 34 can be made smaller. Therefore, an area of a liquid surface in contact with air is small relative to an amount of semen. Then, lowering in performance of semen due to evaporation of a water content can be prevented so that semen can be stored in a favorable state. Furthermore, opening portion 323 in fitting portion 32 of inner case 30 can be greater in area than the horizontal cross-section of semen pool 34 so that semen can easily be put into the container. In addition, in taking out semen with a pipet or the like, even when an amount of semen remaining in inner case 30 is small, semen can be stored at bottom portion 342 and can readily be taken out of semen storage container 10 without tilting outer case 20.

Though one embodiment of the present invention has been described above, the present invention is not limited to the embodiment but is susceptible to various modifications without departing from the gist of the present invention.

Figure 3:
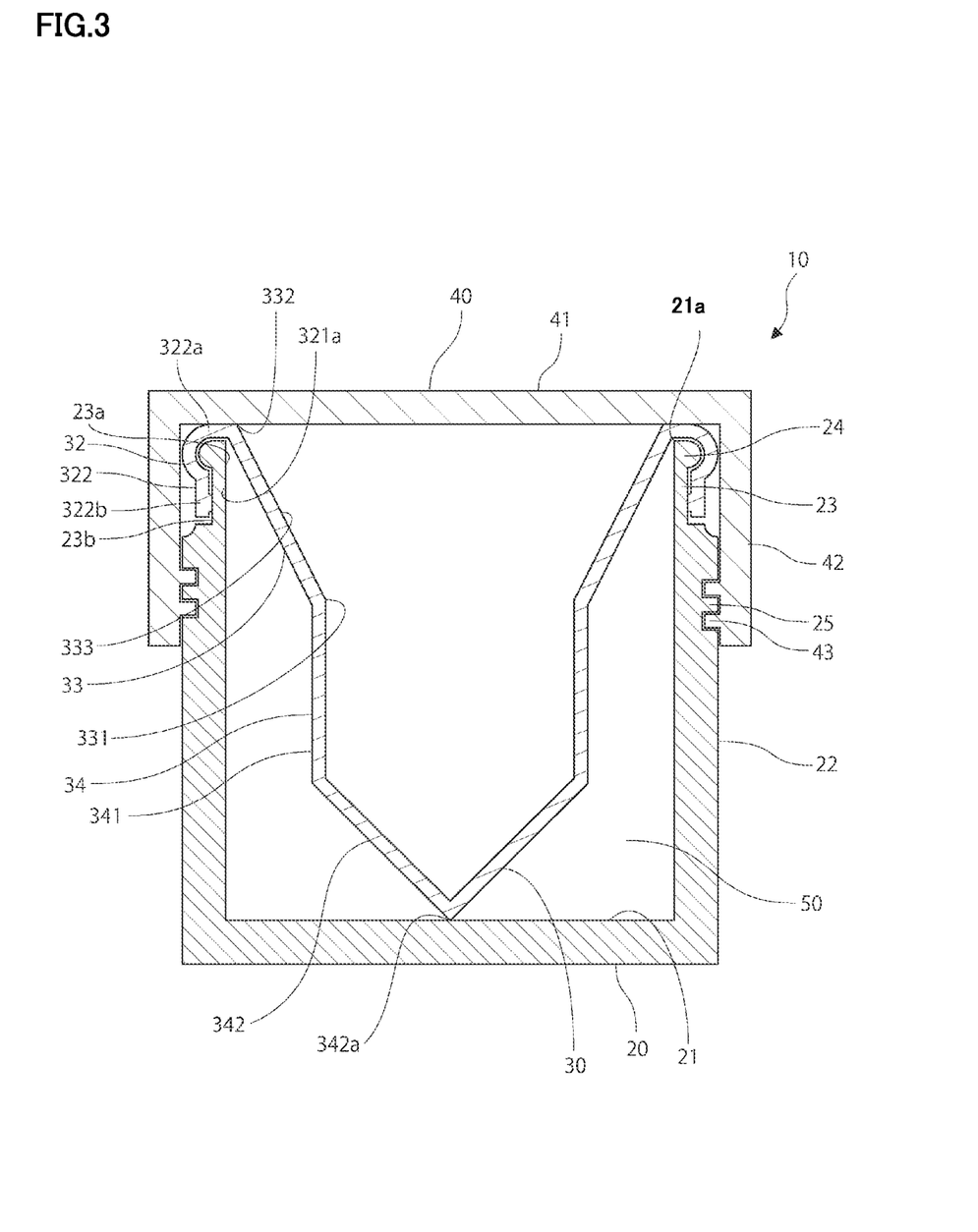
FIG. 3 is a cross-sectional view showing another example of the semen storage container.

FIG. 3 shows another example of semen storage container 10 in the embodiment shown in FIG. 1.

Fitting portion 32 in an embodiment, shown in FIG. 3 is different in not including fitting portion main body 321 in the embodiment in FIG. 1. Specifically, fitting portion 32 is implemented by fold-back portion 322, fold-back portion 322 is formed as being continuous to the upper end of semen guide 33 and folded back toward the outer side of upper end portion 23 of outer case 20, and fitted to upper end portion 23 of outer case 20 from the outer side. Opening portion 332 at the upper end of semen guide 33 is located on the inner side of opening portion 21a at the upper end of outer case 20 and semen is introduced from opening portion 332 in semen guide 33.

Since the construction is otherwise the same as in the embodiment in FIG. 1, corresponding elements have the same reference characters allotted and description is not provided. Fitting portion 32 in the embodiment shown in FIG. 3 may be applied to embodiments in FIGS. 2, 4, and 5.

Figure 4:
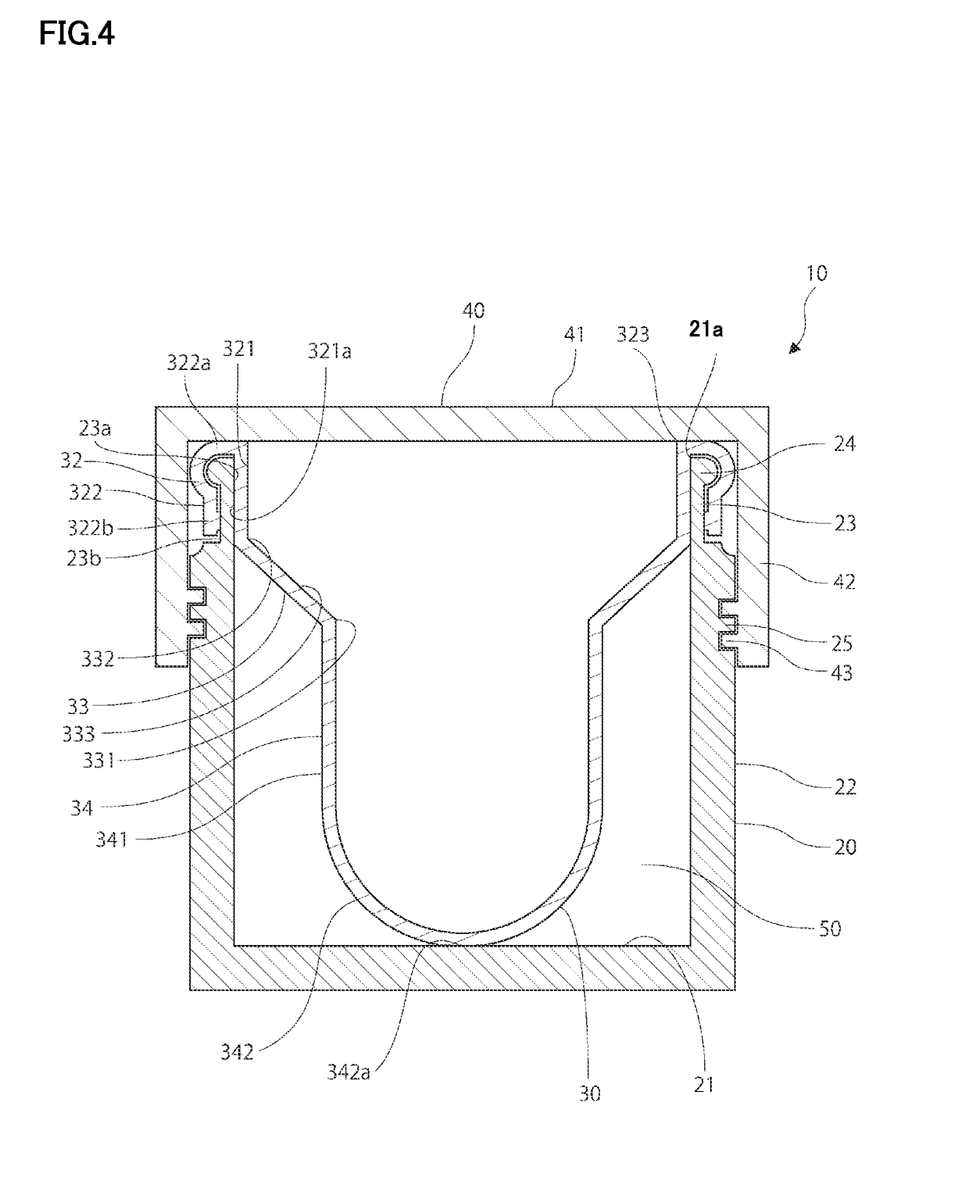
FIG. 4 is a cross-sectional view showing another example of the semen storage container.

FIG. 4 shows another example of semen storage container 10 in the embodiment shown in FIG. 1.

Semen pool 34 in the embodiment shown in FIG. 4 is different in shape of bottom portion 342 from the embodiment in FIG. 1. In the present embodiment, bottom portion 342 is in a hemispherical shape which projects downward.

Since the construction is otherwise the same as in the embodiment in FIG. 1, corresponding elements have the same reference characters allotted and description is not provided. In all other embodiments herein, bottom portion 342 may be in a hemispherical shape projecting downward.

Figure 5:
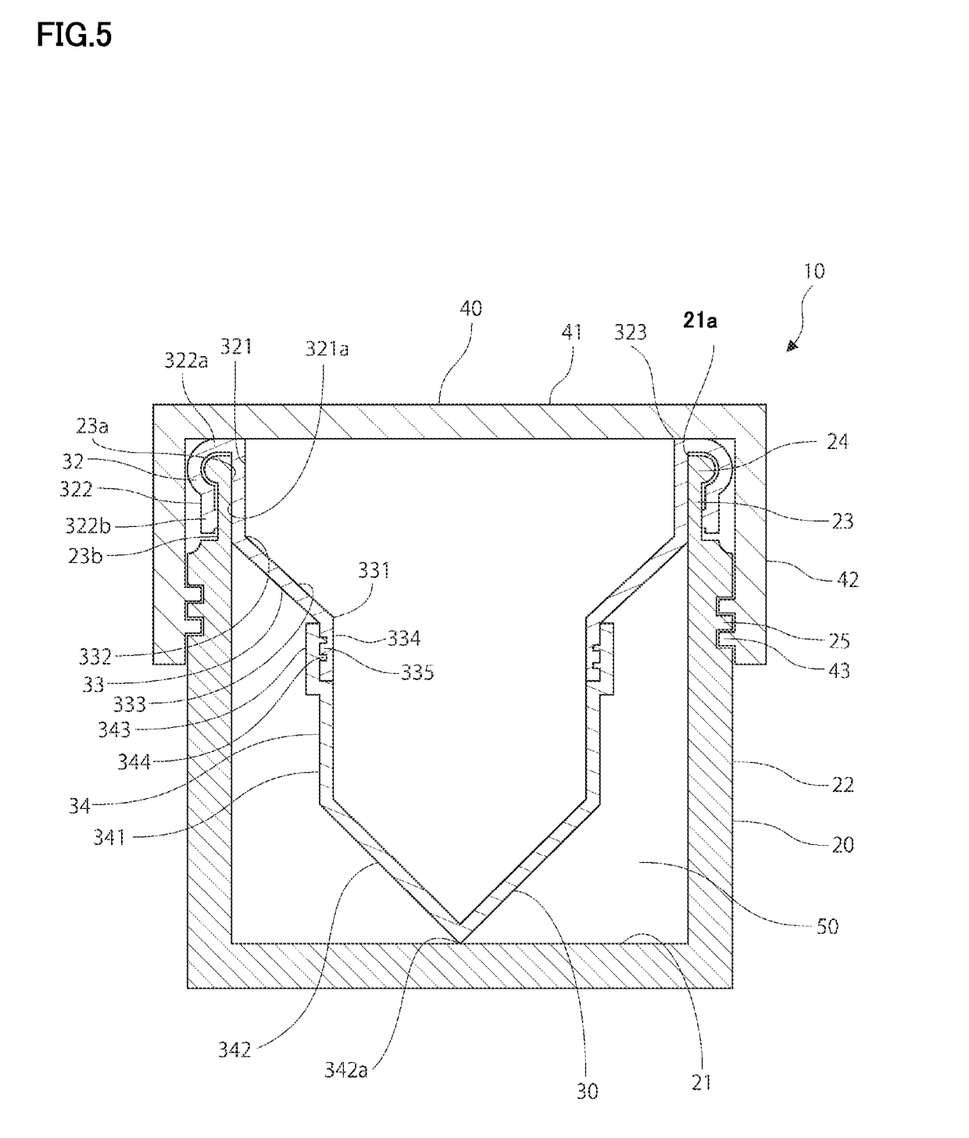
FIG. 5 is a cross-sectional view showing another example of the semen storage container.

FIG. 5 shows another embodiment of semen storage container 10. In the embodiment shown in FIG. 5, semen pool 34 of inner case 30 is separable from semen guide 33. A cylindrical connection portion 334 is formed in opening portion 331 at the lower end of semen guide 33, and a thread 335 for attaching semen pool 34 is formed in an outer circumferential surface of connection portion 334. A cylindrical connection portion 343 having an inner diameter larger than an inner diameter of body portion 341 and substantially as large as an outer diameter of connection portion 334 of semen guide 33 is formed at the upper end portion of semen pool 34, and a thread 344 to be screwed to thread 335 of connection portion 334 of semen guide 33 is formed in an inner circumferential wall of connection portion 343. By fitting connection portion 334 of semen guide 33 to an inner side of connection portion 343 of semen pool 34 and screwing thread 335 and thread 344 together, semen pool 34 is attached to the lower end of semen guide 33. The inner circumferential wall of connection portion 334 of semen guide 33 is continuous to the inner circumferential wall of body portion 341 of semen pool 34. Since the construction is otherwise the same as in the embodiment in FIG. 1, corresponding elements have the same reference characters allotted and description is not provided.

According to the construction, semen pool 34 is shaped and sized in conformity with treatment equipment, inner case 30 can be removed from outer case 20, and semen pool 34 where semen is accommodated is separated from semen guide 33, so that semen pool 34 can directly be set onto the treatment equipment. Since transfer of semen to a test tube does not have to be performed, operations can be more efficient and contamination of semen caused in transfer of semen to the test tube can be prevented.

A lid attachable to connection portion 343 of semen pool 34 may be prepared. When a time period from removable of semen pool 34 from semen storage container 10 until setting thereof onto treatment equipment is long, contamination of semen can be prevented by covering connection portion 343 of semen pool 34 with the lid.

In the present embodiment, connection portion 334 of semen guide 33 is fitted into connection portion 343 of semen pool 34. Connection portion 334 of semen guide 33, however, may be formed to have an inner diameter substantially as large as the outer diameter of connection portion 343 of semen pool 34 so that connection portion 343 of semen pool 34 is fitted into connection portion 334 of semen guide 33. In this case, thread 335 is formed in the inner circumferential wall of connection portion 334 of semen guide 33 and thread 344 is formed in the outer circumferential wall of connection portion 343 of semen pool 34.

Though threads 335 and 344 are formed in connection portion 334 of semen guide 33 and connection portion 343 of semen pool 34, respectively, and semen guide 33 and semen pool 34 are attached to each other by screwing threads 335 and 344 together in the present embodiment, the construction of connection portions 334 and 343 is not limited thereto. For example, connection portion 334 of semen guide 33 and connection portion 343 of semen pool 34 may tightly be fitted to each other.

In the embodiments shown in FIGS. 2 to 4 herein, semen pool 34 may be separable from semen guide 33 by means of connection portions 334 and 343 as in the embodiment in FIG. 5.

In embodiments in FIGS. 1 to 4 and FIG. 6 which will be described later, outer case 20 may be formed to be dividable into an upper portion and a lower portion and semen pool 34 may be separable from semen guide 33 by means of connection portions 334 and 343 as in the embodiment in FIG. 5. In this case, semen pool 34 where semen is accommodated is exposed by separating the lower portion of outer case 20 from the upper portion, so that semen pool 34 is separated from semen guide 33.

Figure 6:
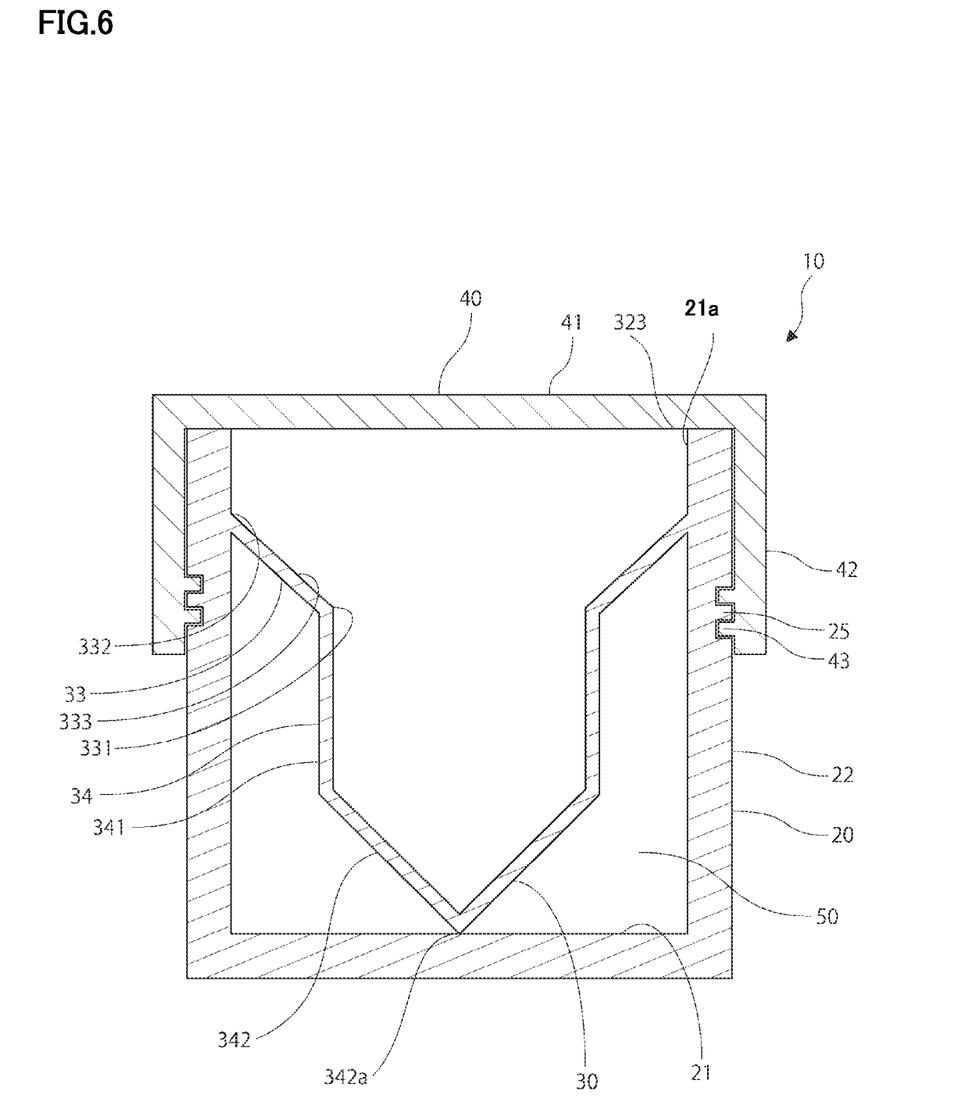
FIG. 6 is a cross-sectional view showing another example of the semen storage container.

FIG. 6 shows another example of semen storage container 10 in the embodiment shown in FIG. 1.

The embodiment shown in FIG. 6 is different from the embodiment in FIG. 1 in that inner case 30 and outer case 20 are integrally formed, upper end portion 23 of outer circumferential wall 22 of outer case 20 is equal in outer diameter to other portions of outer circumferential wall 22, and inner case 30 does not include fitting portion 32 in the embodiment in FIG. 1.

Inner case 30 and outer case 20 are formed by integral injection molding of a synthetic resin, and inner case 30 and outer case 20 are integrally manufactured by fixing opening portion 332 at the upper end of semen guide 33 of inner case 30 to the inner circumferential surface of outer case 20 by welding. Though opening portion 332 of inner case 30 is welded at a position below opening portion 323 at the upper end of outer case 20 in FIG. 6, opening portion 332 of inner case 30 may be welded to opening portion 323 at the upper end of outer case 20.

Since the construction is otherwise the same as in the embodiment in FIG. 1, corresponding elements have the same reference characters allotted and description is not provided.

In all embodiments herein, a part of the outer surface of outer circumferential wall 22 of outer case 20 or a part of the upper surface of top plate portion 41 of lid 40 may be subjected to treatment for allowing writing of a date of collection or a name of a subject.

In all embodiments herein, outer case 20 is not limited to a cylindrical shape but may be, for example, in a hollow prismatic shape. In this case, outer case 20 and lid 40 are locked by engagement hardware provided in outer case 20 and lid 40, rather than threads 25 and 43. The cross-section of the fitting main body of inner case 30, semen guide 33, and semen pool 34 is not limited to an annular shape, but may be, for example, in a quadrangular shape or a polygonal shape.

In all embodiments herein, semen storage container 10 may include an outer container which surrounds outer case 20. The outer container is composed, for example, of foamed plastic, and semen is less likely to be affected by variation in outside temperature by providing the outer container. A heater may be provided in the outer container so that a temperature in semen pool 34 is kept at a room temperature (from 20 degrees to 25 degrees) appropriate for storage of semen.

Figure 7:
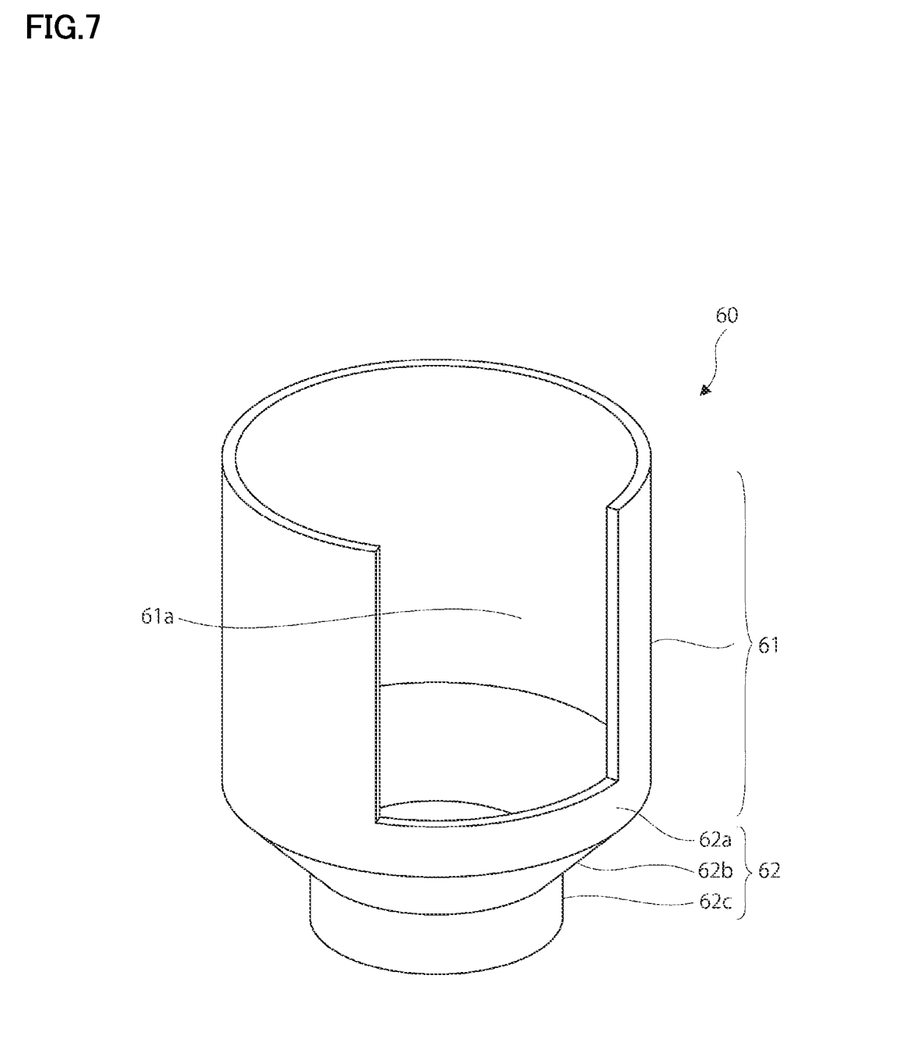
FIG. 7 is a perspective view of a supplemental cover.

Semen storage container 10 may include a cylindrical supplemental cover 60 shown in FIG. 7 for assisting collection of semen. Supplemental cover 60 is used in collecting semen by using semen storage container 10, and includes a cover portion 61 and an insertion portion 62. Cover portion 61 includes a notch 61a provided by cutting a part of a cylindrical body which has open opposing ends along a direction of an axial line and a cross-section along a surface orthogonal to the direction of the axial line in an arc shape.

Insertion portion 62 is provided as a cylindrical body provided as being continuous to cover portion 61 and includes a large diameter portion 62a which continues to cover portion 61, a decreasing diameter portion 62b provided as being continuous to large diameter portion 62a and having an outer diameter continuously decreasing downward in FIG. 7, and a small diameter portion 62c provided as being continuous to decreasing diameter portion 62b. In order to tightly fit insertion portion 62 into inner case 30, large diameter portion 62a, decreasing diameter portion 62b, and small diameter portion 62c of insertion portion 62 have outer diameters substantially equal to the inner diameters of fitting portion main body 321 of inner case 30, semen guide 33, and the upper end portion of semen pool 34, respectively.

An outer circumferential wall of insertion portion 62 is in a shape in conformity with the inner circumferential wall of fitting portion main body 321 of inner case 30, the inner circumferential wall of semen guide 33, and the inner circumferential wall at the upper end portion of semen pool 34.

Figure 8:
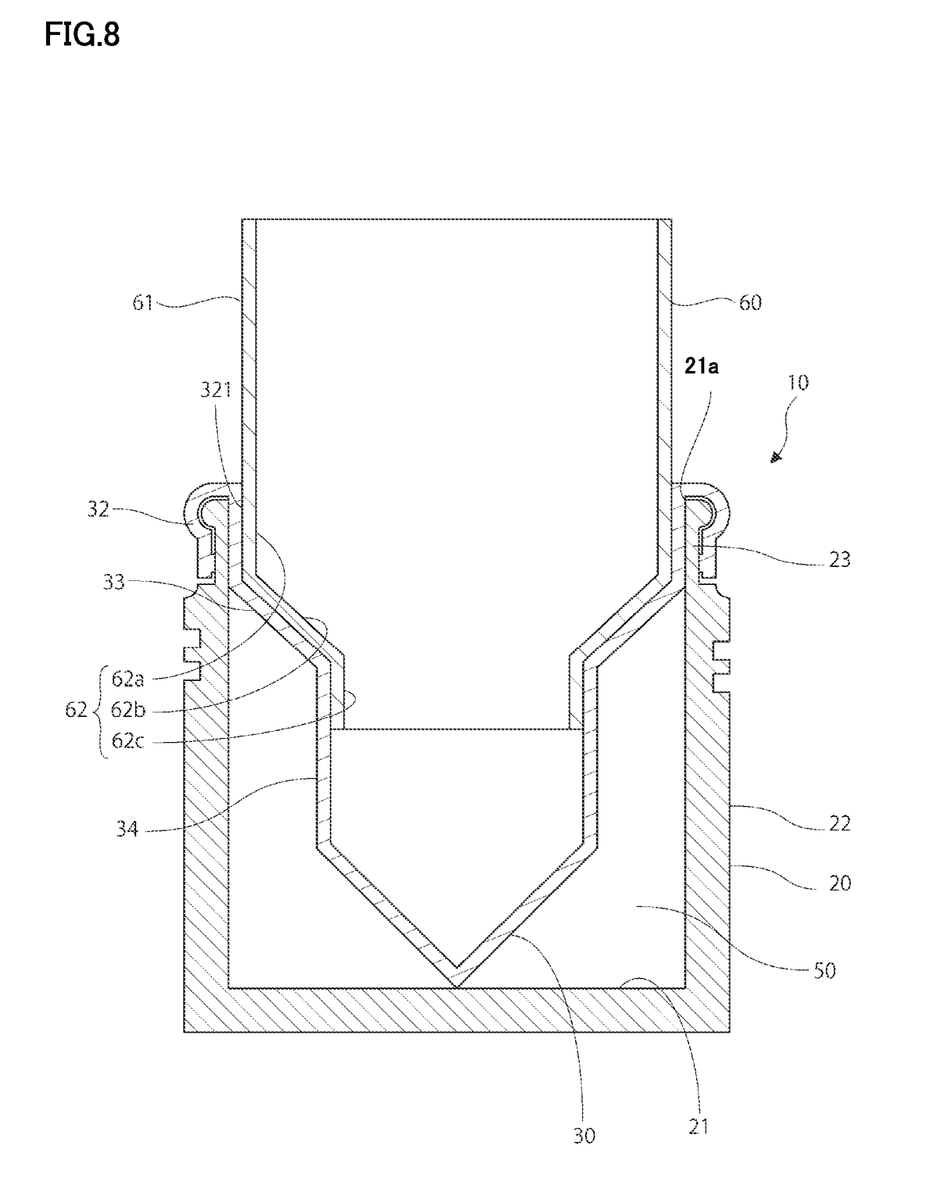
FIG. 8 is a cross-sectional view showing a state that the supplemental cover is supported by an inner case.

As shown in FIG. 8, supplemental cover 60 is attached to inner case 30 while lid 40 of semen storage container 10 is not attached. As insertion portion 62 of supplemental cover 60 is inserted in inner case 30 from above, the outer circumferential wall of insertion portion 62 abuts on the inner circumferential wall of fitting portion main body 321 of inner case 30, the inner circumferential wall of semen guide 33, and the inner circumferential wall of the upper end portion of semen pool 34 so that supplemental cover 60 is supported by inner case 30. Cover portion 61 of supplemental cover 60 protrudes through the opening in inner case 30 at this time, and the lower end of insertion portion 62 is located in the vicinity of the upper end portion of semen pool 34.

In FIG. 8, though supplemental cover 60 is attached to inner case 30 in the embodiment shown in FIG. 1, supplemental cover 60 may be attached to inner case 30 in other embodiments shown in FIGS. 2 to 6.

In collecting semen, a male organ is positioned around the opening and notch 61a of cover portion 61 of supplemental cover 60 to emit semen toward semen pool 34. Droplets of semen impinge on an inner wall surface of cover portion 61 of supplemental cover 60 and falls down to semen pool 34 along an inner circumferential wall of supplemental cover 60.

According to the construction, by attaching supplemental cover 60 to inner case 30, semen can be prevented from scattering in collecting semen, droplets can reliably be recovered, and an amount of semen which can be collected can be increased. With increase in amount of collected semen, sperm in good condition which can be used for assisted reproductive technology is highly likely to be included.

The construction of cover portion 61 of supplemental cover 60 is not limited to the embodiment above and the cover portion should only be constructed to be able to assist semen collection by protruding from the inner case.

The construction of insertion portion 62 of supplemental cover 60 is not limited as above, and the insertion portion may be constructed in any manner so long as supplemental cover 60 can be attached to inner case 30 in a stable manner. For example, insertion portion 62 may include only large diameter portion 62a or may include large diameter portion 62a and decreasing diameter portion 62b. A position of the lower end of insertion portion 62 may be located at any position so long as supplemental cover 60 can be attached to inner case 30 in a stable manner.

REFERENCE SIGNS LIST 10 semen storage container
20 outer case
21a opening portion of outer case
23 upper end portion of outer case
30 inner case
32 fitting portion
323 opening portion
33 semen guide
331 opening portion at lower end
332 opening portion at upper end
333 inclined surface 334 connection portion
34 semen pool
341 cylindrical body portion
342 bottom portion
343 connection portion
50 hermetically sealed space surrounding inner case
60 supplemental cover

The invention claimed is:

1. A semen storage container comprising:
an outer case with a bottom in a cylindrical shape having an open upper end;
an inner case with a bottom, the inner case having an open upper end and being provided on an inner side of the outer case to close an opening portion at the upper end of the outer case; and
a removable lid laid over an upper end portion of the outer case to close an opening portion at the upper end of the inner case,
the inner case including a semen guide which communicates with the opening portion at the upper end of the inner case and has an inner circumferential surface provided as an inclined surface which spreads upward and a cylindrical semen pool which communicates with an opening portion at a lower end of the semen guide and includes a tapered bottom portion,
the inner case is attachable to and removable from the outer case, and
the inner case and the outer case are covered and fixed by the removable lid.

2. The semen storage container according to claim 1, wherein the semen pool has a cylindrical body portion, and the body portion has an upper end continuous to the opening portion at the lower end of the semen guide.

3. The semen storage container according to claim 1, wherein the semen pool has a cylindrical body portion, the body portion has a diameter not greater than 30 mm, and an amount of accommodation of semen is set to be not less than 10 mL and not more than 20 mL.

4. The semen storage container according to claim 1, wherein the semen pool is provided with scales.

5. The semen storage container according to claim 1, wherein a gap between the inner case and the outer case is defined as a hermetically sealed space surrounding the inner case, and any of air, a liquid, a heat insulating material, a thermal storage material, and a heat retention material is accommodated in the hermetically sealed space.

6. The semen storage container according to claim 1, wherein the semen pool is separable from the semen guide,
a first connection portion is provided in the semen pool,
a second connection portion is provided in the semen guide, and
the semen pool is mated to the semen guide by fitting the second connection portion to an inner side of the first connection portion.

7. The semen storage container according to claim 1, the semen storage container further comprising a cylindrical supplemental cover for assisting collection of semen, wherein the supplemental cover includes an insertion portion supported as being inserted into the inner case and a cover portion which protrudes through an opening at the upper end of the inner case.

* * * * *